(12) United States Patent
Lim et al.

(10) Patent No.: US 8,540,725 B2
(45) Date of Patent: Sep. 24, 2013

(54) INSTRUMENTS, IMPLANTS AND METHODS FOR POSITIONING IMPLANTS INTO A SPINAL DISC SPACE

(76) Inventors: Roy Lim, Memphis, TN (US); Steven D. DeRiddar, Bartlett, TN (US)

( * ) Notice: Subject to any disclaimer, the term of this patent is extended or adjusted under 35 U.S.C. 154(b) by 0 days.

(21) Appl. No.: 13/530,776

(22) Filed: Jun. 22, 2012

(65) Prior Publication Data

US 2012/0265211 A1 Oct. 18, 2012

Related U.S. Application Data

(63) Continuation of application No. 12/383,190, filed on Mar. 20, 2009, now Pat. No. 8,231,633, which is a continuation of application No. 11/107,192, filed on Apr. 15, 2005, now Pat. No. 7,575,580.

(51) Int. Cl.
*A61B 17/88* (2006.01)

(52) U.S. Cl.
USPC .......................................................... 606/99

(58) Field of Classification Search
USPC ..... 606/86 A, 86 R, 99, 104, 279; 623/17.11
See application file for complete search history.

(56) References Cited

U.S. PATENT DOCUMENTS

| | | | |
|---|---|---|---|
| 4,457,306 A | 7/1984 | Borzone | |
| 5,782,830 A | 7/1998 | Farris | |
| 6,159,215 A | 12/2000 | Urbahns et al. | |
| 6,319,257 B1 | 11/2001 | Carignan et al. | |
| 6,428,544 B1 | 8/2002 | Ralph et al. | |
| 6,478,801 B1 | 11/2002 | Ralph et al. | |
| 6,527,773 B1 | 3/2003 | Lin et al. | |
| 6,562,072 B1 | 5/2003 | Fuss et al. | |
| 6,569,168 B2 | 5/2003 | Lin | |
| 6,579,318 B2 | 6/2003 | Varga et al. | |
| 6,585,749 B2 | 7/2003 | Hanson | |
| 6,599,294 B2 | 7/2003 | Fuss et al. | |
| 6,613,090 B2 | 9/2003 | Fuss et al. | |
| 6,648,915 B2 | 11/2003 | Sazy | |
| 6,666,866 B2 | 12/2003 | Martz et al. | |
| 6,712,819 B2 | 3/2004 | Zucherman et al. | |
| 6,719,794 B2 | 4/2004 | Gerber et al. | |
| 6,733,504 B2 | 5/2004 | Lin et al. | |
| 6,746,454 B2 | 6/2004 | Winterbottom et al. | |
| 7,060,073 B2 | 6/2006 | Frey et al. | |
| 7,115,132 B2 | 10/2006 | Errico et al. | |
| 7,361,193 B2 | 4/2008 | Frey et al. | |
| 2001/0021853 A1 | 9/2001 | Heckele et al. | |
| 2002/0065558 A1 | 5/2002 | Varga et al. | |
| 2002/0065560 A1 | 5/2002 | Varga et al. | |
| 2002/0165550 A1 | 11/2002 | Frey et al. | |
| 2003/0014057 A1 | 1/2003 | Ralph et al. | |
| 2003/0014115 A1 | 1/2003 | Ralph et al. | |
| 2003/0023245 A1 | 1/2003 | Ralph et al. | |
| 2003/0083747 A1 | 5/2003 | Winterbottom et al. | |
| 2003/0130667 A1 | 7/2003 | Lin | |
| 2003/0135275 A1 | 7/2003 | Garcia et al. | |
| 2003/0139813 A1 | 7/2003 | Messerli et al. | |

(Continued)

FOREIGN PATENT DOCUMENTS

| | | |
|---|---|---|
| WO | WO 02/17823 A1 | 3/2002 |
| WO | WO 03/037228 A2 | 5/2003 |

*Primary Examiner* — Mary C. Hoffman
*Assistant Examiner* — Tara Carter

(57) ABSTRACT

Instruments, implants and methods are provided for positioning spinal implants in a spinal disc space between adjacent vertebrae. The instruments provide a low profile engagement with the implants and facilitate insertion while minimizing tissue retraction and exposure of the tissue and neural elements to the instrumentation in the approach to the disc space.

20 Claims, 11 Drawing Sheets

(56) References Cited

U.S. PATENT DOCUMENTS

| | | |
|---|---|---|
| 2003/0149438 A1 | 8/2003 | Nichols et al. |
| 2003/0208203 A1 | 11/2003 | Lim et al. |
| 2004/0153065 A1 | 8/2004 | Lim |
| 2005/0027360 A1 | 2/2005 | Webb et al. |
| 2005/0038431 A1 | 2/2005 | Bartish et al. |
| 2005/0055031 A1 | 3/2005 | Lim |
| 2005/0203538 A1 | 9/2005 | Lo et al. |
| 2006/0229627 A1 | 10/2006 | Hunt et al. |
| 2006/0241761 A1 | 10/2006 | Gately |
| 2006/0264968 A1 | 11/2006 | Frey et al. |
| 2007/0016221 A1 | 1/2007 | Beyersdorff et al. |

INSTRUMENTS, IMPLANTS AND METHODS FOR POSITIONING IMPLANTS INTO A SPINAL DISC SPACE

CROSS-REFERENCE TO RELATED APPLICATIONS

The present application is a continuation of U.S. patent application Ser. No. 12/383,190 filed on Mar. 20, 2009 now allowed, which is a continuation of U.S. patent application Ser. No. 11/107,192, filed Apr. 15, 2005, which is now issued as U.S. Pat. No. 7,575,580. The referenced applications each being hereby incorporated by reference herein in their respective entireties.

BACKGROUND

Normal intervertebral discs between endplates of adjacent vertebrae distribute forces between the vertebrae and cushion vertebral bodies. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most surgical corrections of a disc space include a discectomy, which can be followed by restoration of normal disc space height and bony fusion of the adjacent vertebrae to maintain the disc space height.

Access to a damaged disc space may be accomplished from several approaches to the spine. One approach is to gain access to the anterior portion of the spine through a patient's abdomen. However, extensive vessel retraction is often required and many vertebral levels are not readily accessible from this approach. A posterior approach may also be utilized. This approach typically requires that both sides of the disc space on either side of the spinal cord be surgically exposed, which may require a substantial incision or multiple access locations, as well as extensive retraction of the spinal cord. To alleviate problems associated with both anterior and posterior approaches to the spine, a postero-lateral approach to the disc space may be utilized.

There remains a need for improved instruments, implants and techniques for use in a postero-lateral approach to a spinal disc space that facilitate disc space preparation and implant insertion to provide bilateral stability to the subject disc space.

SUMMARY

There are provided instruments, implants and methods useful for implant insertion from a postero-lateral approach to the spinal disc space, although application with other approaches are also contemplated.

DETAILED DESCRIPTION OF THE ILLUSTRATED EMBODIMENTS

Figure 2:
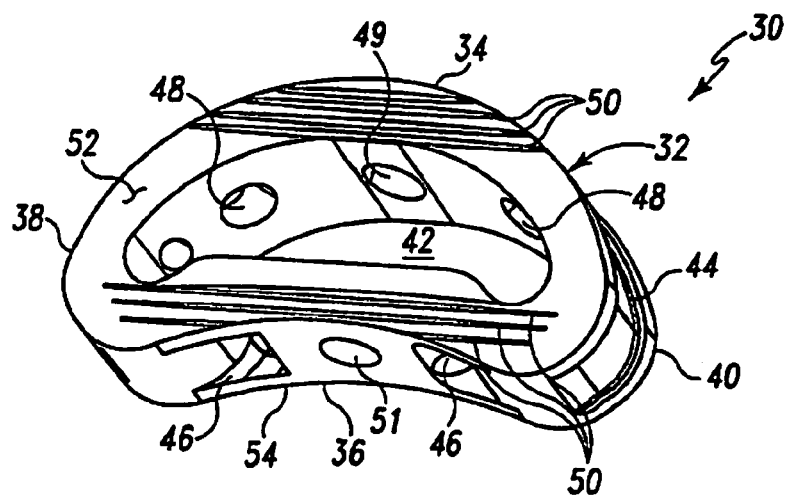
FIG. 2 is an enlarged perspective view of the implant of FIG. 1.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

Instruments, implants and techniques provide and facilitate implant insertion into a spinal disc space through a single opening and positioning of the implant so that it provides balanced, bi-lateral support of the adjacent vertebrae. The instruments and implants can be employed in postero-lateral approaches to the disc space to obtain proper positioning of the implant in the portion of the disc space most distal from the postero-lateral opening. The instruments and implants facilitate moving the implant across the disc space to the distal portion of the disc space so that the implant extends between distal and proximal portions of the disc space to provide bi-lateral support of the adjacent vertebrae. The inserter instruments provide a low profile engagement with the implant to minimize the footprint of the assembly and minimize exposure and retraction of tissue and neural elements to accommodate implant insertion.

Figure 1:
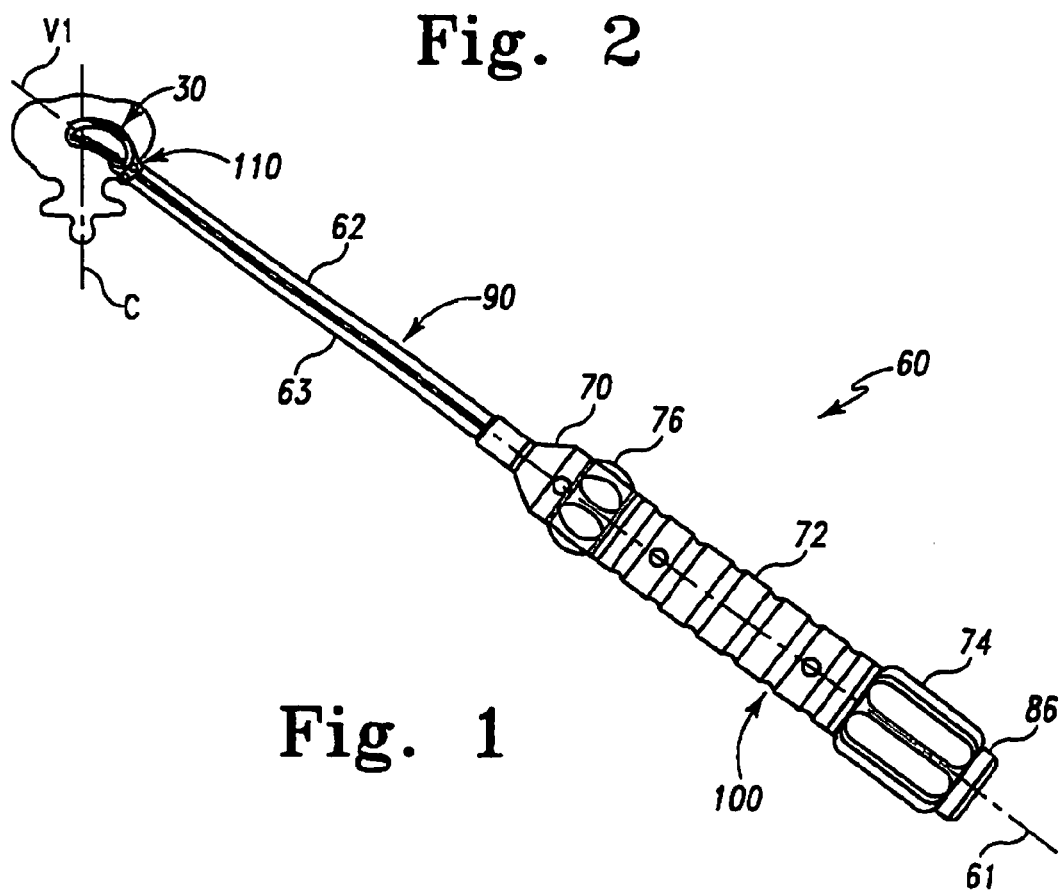
FIG. 1 is a plan view of an inserter instrument and an implant in an initial position in a spinal disc space.
Figure 3:
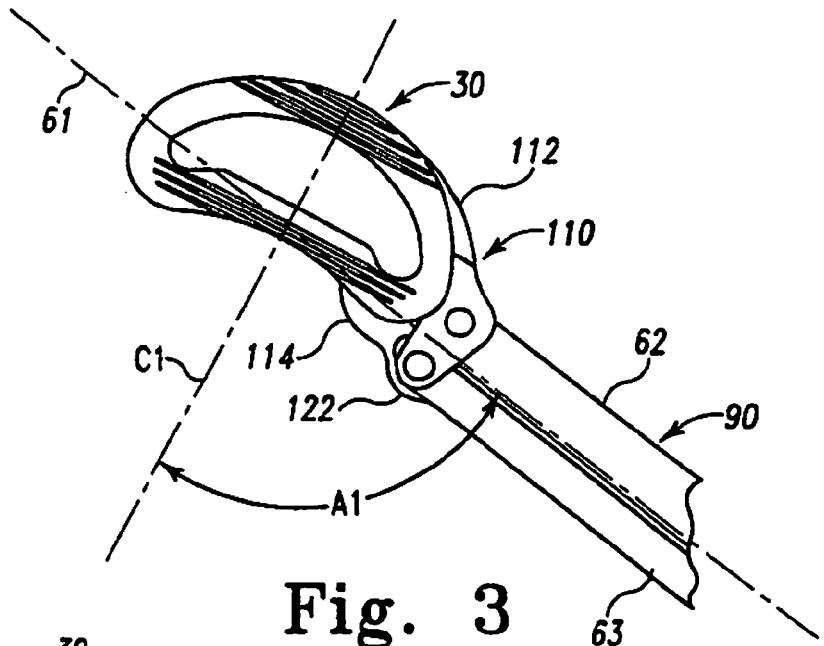
FIG. 3 is an enlarged plan view showing the implant engaged with the distal end of the inserter instrument in the initial position of FIG. 1.

In FIGS. 1 and 3 there is shown one embodiment inserter instrument 60 engaged to a trailing end of implant 30 at the distal end of inserter instrument 60. A vertebral body V1 is shown with the implant 30 positioned in a disc space adjacent thereto in an initial position. In the initial position, implant 30 is inserted into the disc space while inserter instrument 60 maintains implant 30 in general alignment along longitudinal axis 61 of inserter instrument 60. In postero-lateral procedures, implant 30 extends obliquely to sagittal plane C of the patient when in the initial position.

Figure 4:
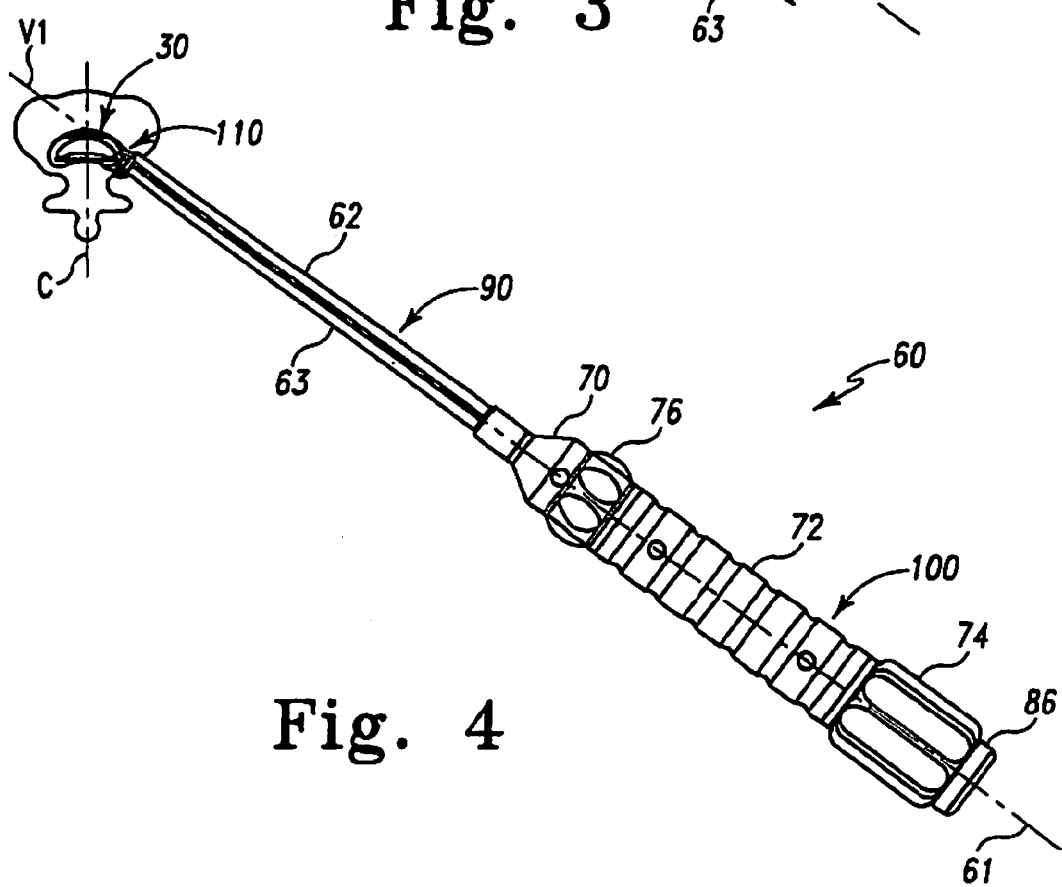
FIG. 4 is a plan view of the inserter instrument and the implant in a final position in the spinal disc space.
Figure 5:
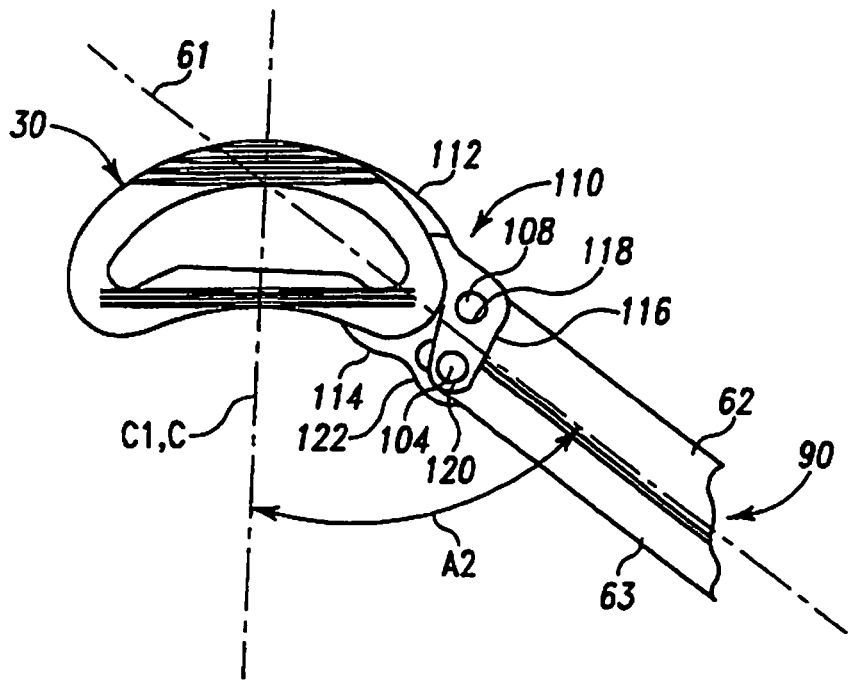
FIG. 5 is an enlarged plan view showing the implant engaged with the distal end of the inserter instrument in the final position of FIG. 4.

In FIGS. 4 and 5, inserter instrument 60 has been manipulated to reposition implant 30 to a final position for implantation in the disc space. In the orientation of the final position, implant 30 is substantially obliquely oriented to longitudinal axis 61 of inserter instrument 60. Furthermore, implant 30 includes an axis of symmetry C1. Axis C1 is oriented so that it is aligned along or generally parallel to sagittal plane C of the patient. In the final position, implant 30 extends across sagittal plane C and contacts the adjacent vertebral endplates to provide balanced bi-lateral support of the adjacent vertebrae. Inserter instrument 60 can then be disengaged from implant 30 and withdrawn from the patient.

The disc space can be accessed and prepared from the postero-lateral approach using spreaders, cutters, chisels, reamers, and other instruments to prepare the disc space and adjacent vertebral endplates to receive implant 30. Examples of such instruments and techniques are discussed in U.S. Patent Application Publication No. 2002/0165550, published Nov. 7, 2002, which is incorporated herein by reference in its entirety.

One embodiment of implant 30 is shown in further detail in FIG. 2, it being understood that any suitable implant can be engaged to inserter instrument 60. Implant 30 includes a body formed by a wall 32 extending about a central cavity 42. Cavity 42 extends between and opens at an upper bearing surface 52 and a lower bearing surface 54. Upper and lower bearing surfaces 52, 54 contact the adjacent vertebral endplates to support the adjacent vertebrae when implant 30 is implanted in the spinal disc space. Surfaces 52, 54 may include grooves 50 formed therein to facilitate engagement with the vertebral endplates and resist the implant from migrating in the disc space. Other surface features are also contemplated, including teeth, spikes, knurlings, peeks and valleys, and other projections and/or recesses.

Implant 30 includes convexly curved anterior wall portion 34 and an opposite concavely curved posterior wall portion 36. Wall portions 34, 36 are connected by a convexly curved leading end wall portion 38 and a convexly curved trailing end wall portion 40. The overall shape of wall 32 provides a banana, kidney or boomerang type shape that facilitates placement of implant 30 along a non-linear insertion path in the disc space from the proximal postero-lateral opening to a distal portion of the disc space opposite the postero-lateral opening. In the implanted position, posterior wall portion 36 is oriented toward the spinal foramen. The anterior wall portion 34 extends anteriorly to provide anterior support of the vertebrae. The elongated shape of implant 30 facilitates placement through the postero-lateral opening while minimizing the retraction of tissue and neural elements needed to accommodate placement of the implant through the postero-lateral approach. It should be understood the leading end wall portion 38 can be a trailing end wall portion, and trailing end wall portion 40 can be a leading end wall portion, in situations where wall portion 38 is engaged with an inserter instrument and wall portion 40 is first inserted into the disc space through the postero-lateral opening.

A central opening 49 in anterior wall portion 34 and a central opening 51 in posterior wall portion 36 provide avenues for bone growth into cavity 42. Implant 30 further includes a recessed area 44 that extends around the trailing end wall portion 40 and along at least a portion of the length of anterior wall portion 34. A receptacle 46 is formed in posterior wall portion 36. As discussed further below, the recessed area 44 and receptacle 46 are configured for engagement by respective portions of a grasper assembly 110 of inserter instrument 60. Lateral pin holes 48 in recessed areas 44 of anterior wall portion 34 can provide additional areas for engagement by the inserter instrument.

As shown in FIG. 1, inserter instrument 60 includes a shaft assembly 90 and a proximal handle assembly 100 extending along longitudinal axis 61. Implant 30 is engaged to inserter instrument 60 with grasper assembly 110 at the distal end of shaft assembly 90. Handle assembly 100 is operably coupled with grasper assembly 110 through shaft assembly 90 to remotely manipulate grasper assembly 110 to grasp and release implant 30 from inserter instrument 60. Grasper assembly 110 is also remotely operable to reposition implant 30 relative to longitudinal axis 61 from an initial position, shown in FIGS. 1 and 3, to a final implanted position, shown in FIGS. 4-5.

Shaft assembly 90 of inserter instrument 60 includes a first shaft 62 and a second shaft 63. Second shaft 63 extends along and parallel to first shaft 62, and includes a C-shaped side oriented toward a C-shaped side of first shaft 62. The C-shaped sides together form a passage that receives a locking shaft 68 (FIG. 6.) therein. Shaft assembly 90 further includes a hub 70 at a proximal end thereof adjacent handle assembly 100. Second shaft 63 is engaged to hub 70. First shaft 62 and locking shaft 68 extend through hub 70 and into handle assembly 100

Handle assembly 100 includes an outer cylindrical handle member 72 have grip-enhancing external surface features. A rotatable articulator driver 74 is between a proximal end of handle member 72 and a proximal end member 86. Handle assembly 100 further includes a rotatable lock driver 76 at a distal end of handle member 72 between handle member 72 and hub 70. Drivers 74, 76 each include a series of radial protuberances and valleys between protuberances to enhance the ability to grip and apply the necessary force to rotate drivers 74, 76.

Figure 13:
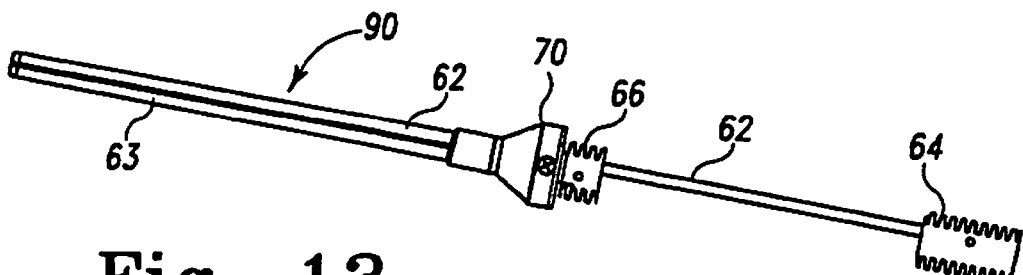
FIG. 13 is a top plan view of a portion of the shaft assembly and an interior portion of a handle assembly of the inserter instrument.

Further details of handle assembly 100 are shown in FIGS. 13-17. In FIG. 13 handle member 72, drivers 74, 76, and second shaft 63 are removed. Locking shaft 68 extends through hub 70 to a lock screw 66 at a proximal end of locking shaft 68. First shaft 62 extends through hub 70 and also through lock screw 66 to an articulator screw 64 at a proximal end of first shaft 62. Screws 64, 66 are linearly movable to linearly move the respective shafts 62, 68 in response to rotation of the respective drivers 74, 76 thereabout.

Figure 14:
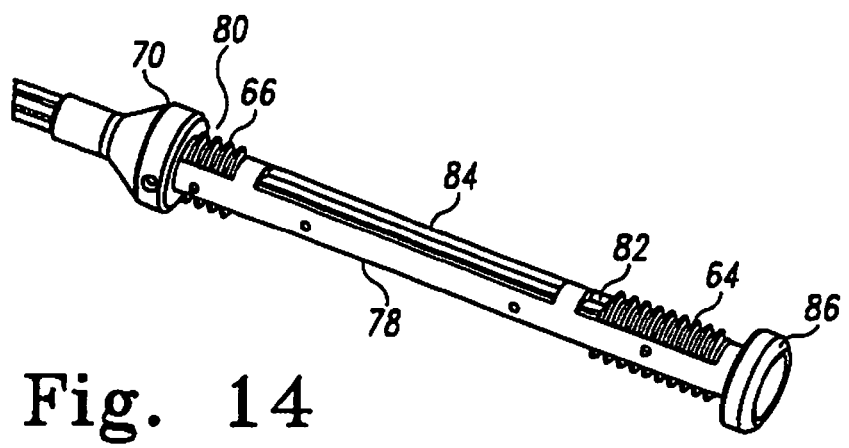
FIG. 14 is a perspective view of the interior portion of the handle assembly shown in FIG. 13 including a frame of the handle assembly.

In FIG. 14, a frame 78 is positioned about shafts 62, 68 and screws 64, 66. Frame 78 includes a distal slot 80 that receives lock screw 66, a proximal slot 82 that receives articulator screw 64, and an intermediate slot 84 therebetween. Slots 80, 82 are elongated sufficiently to allow proximal and distal translation of screws 64, 66 to remotely manipulate grasper assembly 110. End member 86 at the proximal end of frame 78 can receive and transmit impaction forces to facilitate insertion of the implant into the disc space.

Figure 15:
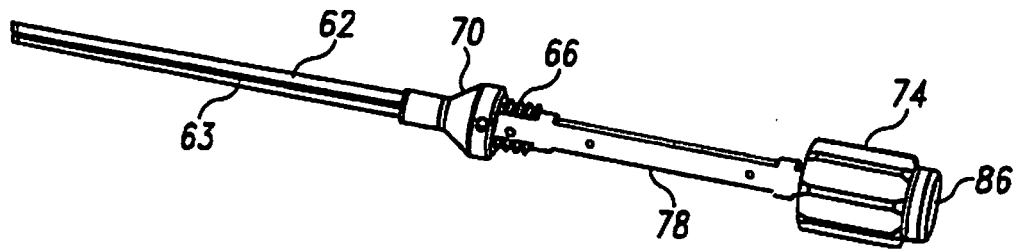
FIG. 15 is the view of FIG. 13 including the frame of FIG. 14 and also an articulating driver of the handle assembly.

In FIG. 15 there is shown articulator driver 74 rotatably positioned about and threadingly engaged to articulator screw 64. Rotation of articulator driver 74 about screw 64 linearly advances first shaft 62 in a proximal or distal direction, depending on the direction of rotation. The linear movement of first shaft 62 in turn articulates grasper assembly 110 between the initial position and the final position, as discussed above and as discussed further below.

Figure 7:
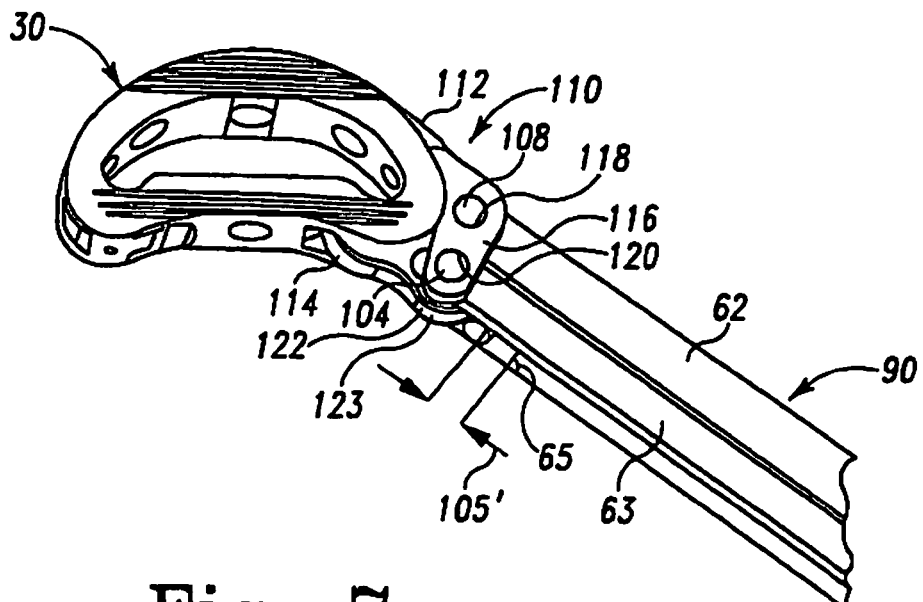
FIG. 7 is a perspective view of the distal end of the inserter instrument in an engaged position with the implant and the implant oriented in the final position.
Figure 8:
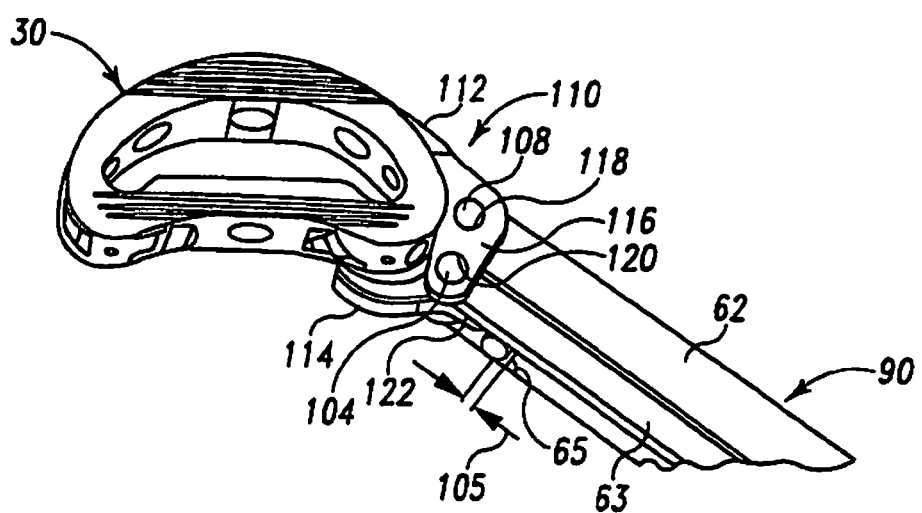
FIG. 8 is a perspective view of the distal end of the inserter instrument in a release position with the implant and the implant oriented in the final position.
Figure 9:
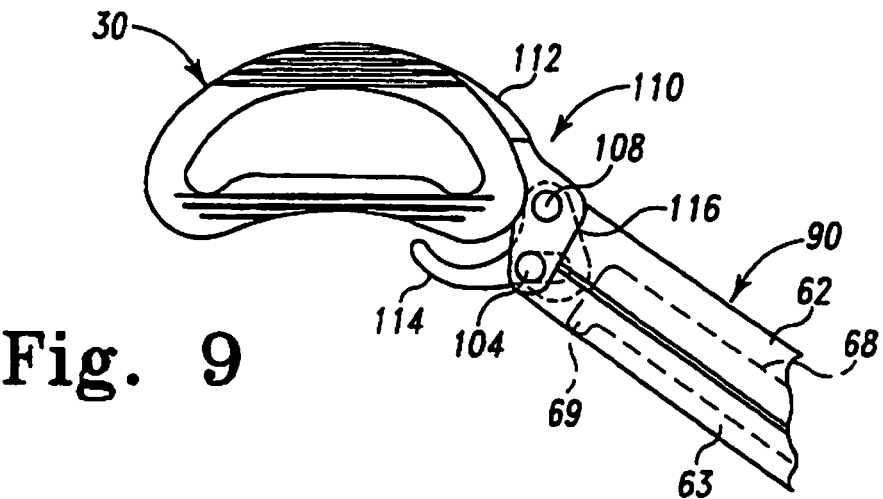
FIG. 9 is a top plan view of the distal end of the inserter instrument in a release position immediately after placing the implant in the final position.
Figure 10:
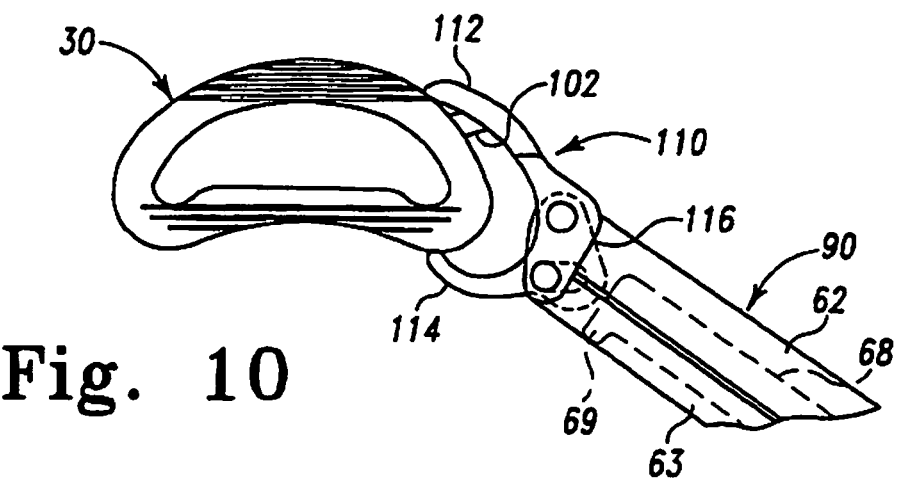
FIG. 10 is a top plan view of the distal end of the inserter instrument in the release position and the inserter withdrawn proximally from the implant oriented in the final position.
Figure 11:
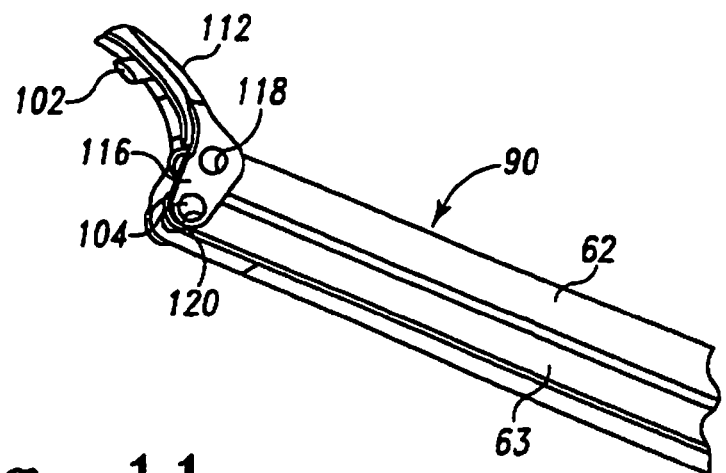
FIG. 11 is a perspective view of the distal end of the inserter instrument with the posterior arm removed and the anterior arm in the initial position.
Figure 12:
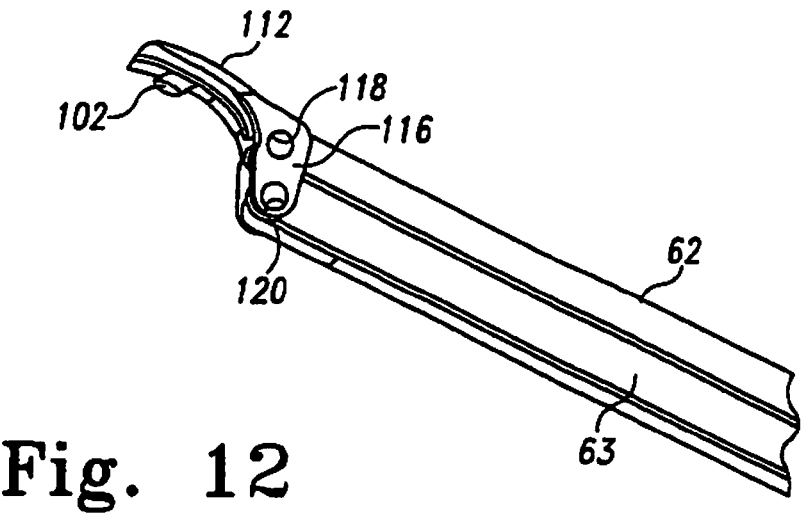
FIG. 12 is a perspective view of the distal end of the inserter instrument with the posterior gripping arm removed and the anterior arm in the final position.
Figure 16:
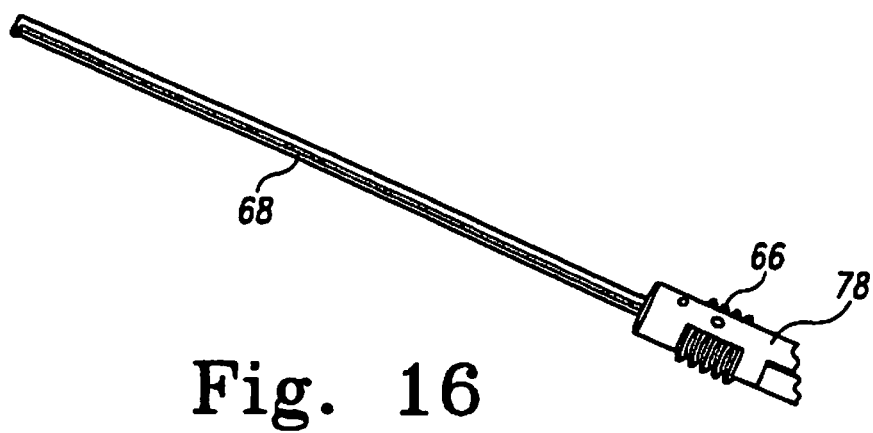
FIG. 16 is a perspective view showing a portion of the shaft assembly with a hub removed and a proximal portion of the interior of the handle assembly.
Figure 17:
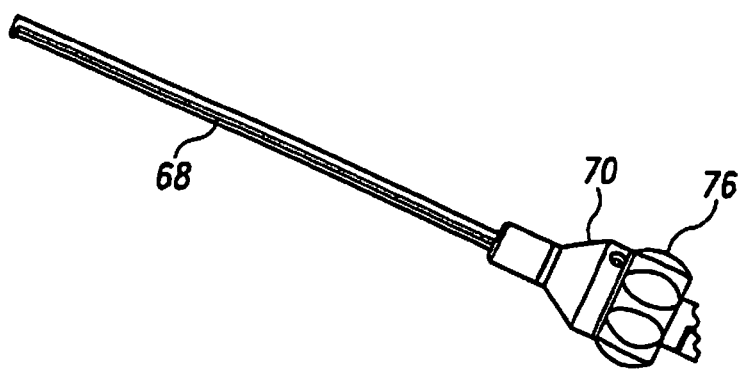
FIG. 17 is the view of FIG. 16 with a lock driver engaged about a lock screw of the handle assembly.
Figure 18:
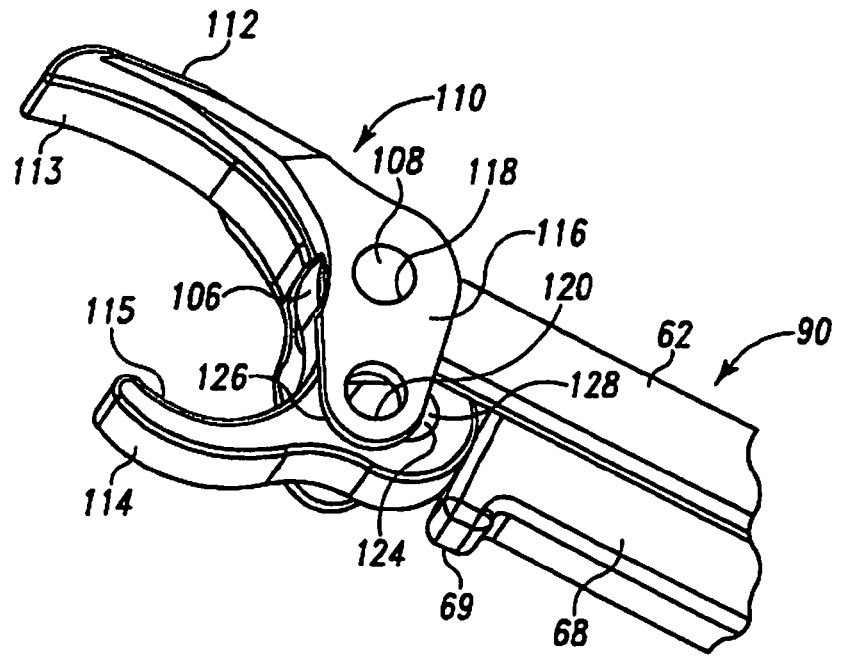
FIG. 18 is a perspective view of the distal portion of the inserter instrument in the release position with the implant removed.

In FIG. 16 there is shown lock screw 66 and shafts 62, 63 are removed. In FIG. 17 lock driver 76 is threadingly engaged to and rotatably positioned about lock screw 66. Rotation of lock driver 76 linearly advances locking shaft 68 in a proximal or distal direction, depending on the direction of rotation. The linear movement of locking shaft 68 in turn manipulates grasper assembly 110 between a release position and an engaged position relative to the implant positioned therein. In the release position, grasper assembly 110 is opened to receive or release the implant, as shown in FIGS. 8 and 18, for example. In the engaged position, the implant positioned in grasper assembly 110 is engaged by the grasper assembly 110 and to couple the implant to inserter instrument 60, as shown in FIGS. 7 and 19, for example.

Figure 19:
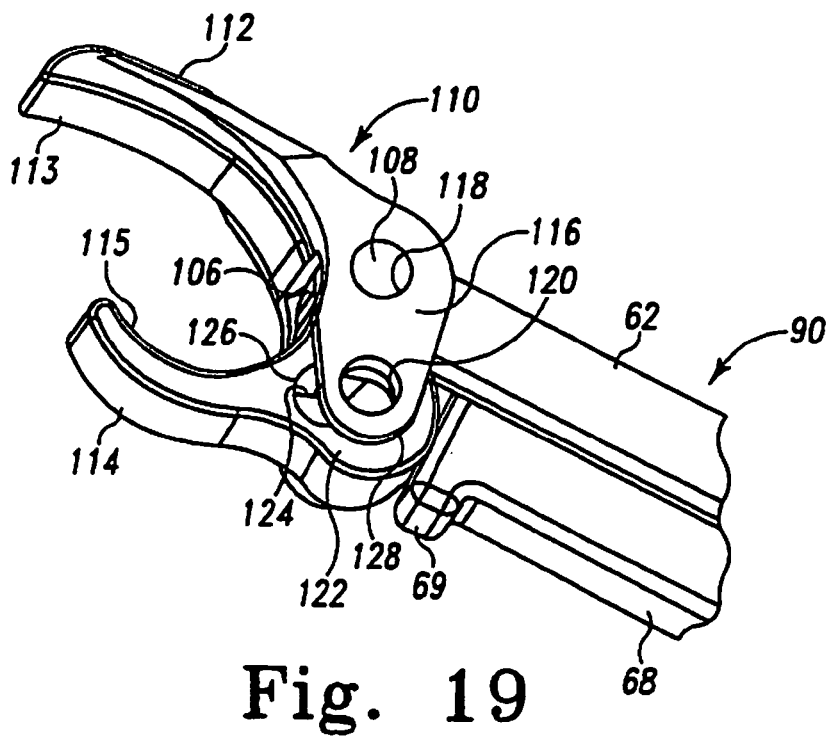
FIG. 19 is a perspective view of the distal portion of the inserter instrument in the engaged position with the implant removed.
Figure 20:
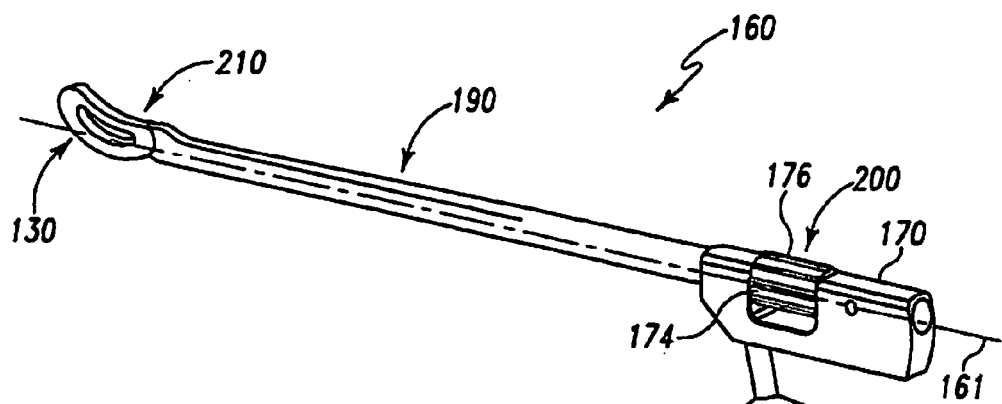
FIG. 20 is a perspective view of another embodiment inserter instrument and implant.

As shown in FIGS. 6-12 and 18-19, grasper assembly 110 includes a first arm 112 and a second arm 114. First arm 112 includes a concavely curved inner surface 113, and second arm 114 includes a second concavely curved inner surface 115. Surfaces 113, 115 are oriented toward one another, and are shaped to conform to the outer wall surfaces of implant 30 about trailing end wall portion 40 and in recessed area 44 and receptacle 46, respectively. First arm 112 may include a pin 102 that is positionable into a pin hole 48 in recessed area 44 to further engage implant 30 to grasper assembly 110 and to maintain the implant in engagement therewith. Other embodiments contemplated that pin 102 is not provided, such as shown in FIGS. 18 and 19.

First arm 112 includes a proximal lever portion 116 having a first end 118 pivotally coupled to a distal end of first shaft 62 with a pin 108, and a second end 120 pivotally coupled to a distal end of second shaft 63 with a pin 104. Lever portion 116 includes a forked arrangement for positioning along the outer surfaces of shafts 62, 63 to accommodate placement of a heel portion 122 and toe portion 106 of second arm 114 therebetween.

Figure 6:
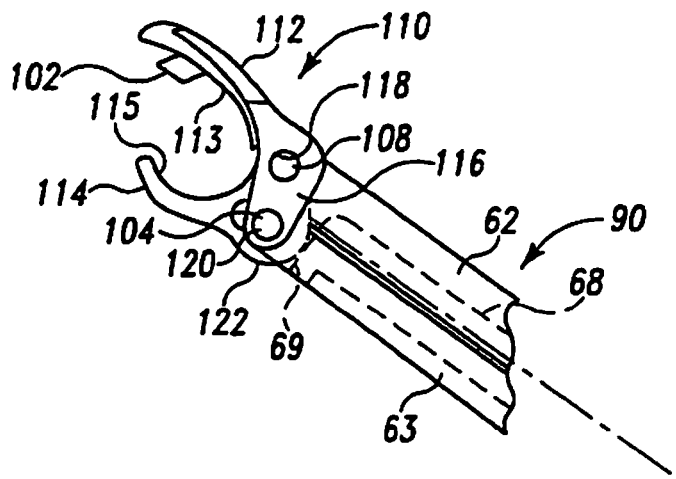
FIG. 6 is a plan view of the distal end of the inserter instrument with the implant removed and with the inserter in the initial position.

Second arm 114 includes proximal heel portion 122 having a bulbous shape positioned in contact with a distal foot 69 of locking shaft 68 (FIGS. 6, 18-19). Heel 122 includes a slotted hole 124 extending between a distal end 126 and a proximal end 128. Pin 104 pivotally engages second end 120 of first grasping arm 112 to the distal end of second shaft 63. Pin 104 also extends through slotted hole 124 to couple second arm 114 to the distal end of second shaft 63 while also allowing limited radial translation of second arm 114 relative to first arm 112. Slotted hole 124 is configured between its distal end 126 and proximal end 128 to allow second arm 114 to move toward and away from first arm 112 to selectively grip and release the implant therebetween. Second arm 114 further includes a toe portion 106 opposite heel portion 122. Toe portion 106 is pivotally coupled with first shaft 62 and first end 118 of first grasping arm 112 with pin 108.

Linear distal movement of first shaft 62 by rotating articulator driver 74 causes distal displacement of first end 118 relative to second end 120, which in turn pivots first arm 112 and second arm 114 about pin 104 and the fixed second shaft 63. This movement in turn moves grasper assembly 110 from its initial position, as shown in FIGS. 1 and 3, to its final position, as shown in FIGS. 4-5. In one embodiment, axis C1 of implant 30 forms an angle A1 (FIG. 3) with longitudinal axis 61 in the initial position, and an angle A2 (FIG. 5) in the final position. In one specific embodiment, angle A1 is about 80 degrees to generally orient implant 30 along axis 61. Angle A2 is about 55 degrees to orient implant 30 in a substantially oblique orientation to axis 61. Other embodiments contemplate other angular orientations, ranging from 70 degrees to 110 degrees for angle A1 and ranging from 35 degrees to 75 degrees for angle A2. Still other embodiments contemplate other angular ranges for angles A1 and A2.

Arms 112, 114 are further moveable to grip and release implant 30 from therebetween. In the release position, shown in FIGS. 8-10 and 18, pin 104 is adjacent distal end 126 of slotted hole 124 and foot 69 of locking shaft 68 is moved distally to a location spaced a distance 105 from an end wall 65 of a slot in second shaft 63. This allows second arm 114 to rotate away from first arm 112. To move arms 112, 114 to the engaged position, foot 69 is advanced distally with distal movement of locking shaft 68 by rotation of locking driver 76. As shown in FIG. 7, distal movement of foot 69 displaces it a second greater distance 105' from end wall 65 of second shaft 63, and locking shaft 68 articulates second arm 114 toward first arm 112. This movement positions pin 104 adjacent the proximal end 128 of slotted hole 124. The articulation of second arm 114 in the clockwise direction can be continued to firmly grasp implant 30 between first and second arms 112, 114 as shown in FIGS. 5 and 7, for example.

Heel portion 122 includes a circular outer perimeter 123 that contacts foot 69 in the engaged position. While in the engaged position, grasper assembly 110 can be moved from the initial position to the implanted position. During this movement, the circular perimeter 123 allows foot 69 to maintain contact with heel portion 122 and maintain arms 112, 114 in the engaged position with implant 30.

In use, arms 112, 114 of inserter instrument 60 are placed in the release position to receive implant 30 therebetween. Lock driver 76 is rotated to move arms 112, 114 to the engaging position to firmly grip implant 30 with grasping assembly 110 in the initial position. Implant 300 is delivered to the postero-lateral opening in the disc space and the leading end of the implant is positioned through the opening while being maintained in the initial position. The implant is advanced in the initial position along axis 61 in a direction substantially obliquely oriented to sagittal plane C until the trailing end of implant 30 is positioned in the disc space. Impaction forces can be delivered to the proximal end of the inserter instrument if necessary.

When implant 30 is in the appropriate position in the disc space, articulator driver 74 can be rotated to manipulate first shaft 62 and grasper assembly 110 to move implant 30 from the initial position to the final position in the disc space. In the final position, axis C1 of implant 30 is oriented along or generally parallel to sagittal plane C. Lock driver 76 can then be rotated to move locking shaft 68 proximally to allow arms 112, 114 to the release position for withdrawal of inserter instrument from the disc space.

FIGS. 20-23 show another embodiment implant and implant inserter. Implant inserter 160 includes an elongated shaft assembly 190, a grasper assembly 210 at a distal end of shaft assembly 190, and a handle assembly 200 at a proximal end of shaft assembly 190. Implant 130 is releasably engageable at the distal end of shaft assembly 190 with grasper assembly 210. Handle assembly 200 is operable to manipulate grasper assembly 210 to grasp and release the implant 130, and to deliver implant 130 to the spinal disc space. While specific applications in postero-lateral approaches to the disc space are contemplated as discussed above, other approaches to the disc space are also contemplated.

Figure 21:
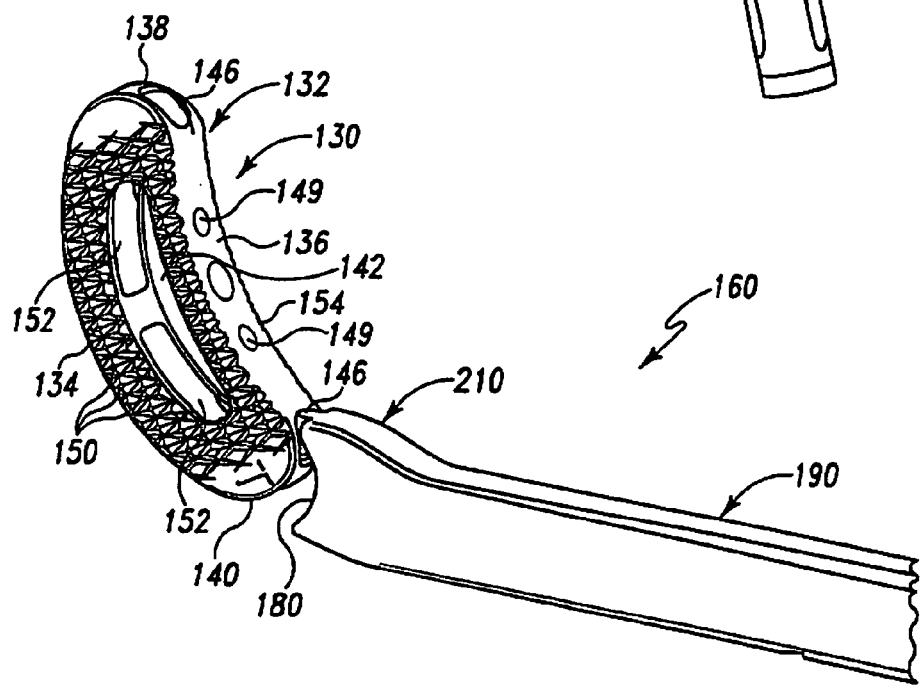
FIG. 21 is a perspective view of a distal portion of the inserter instrument and the implant of FIG. 20 with the implant partially engaged to the inserter instrument.
Figure 22:
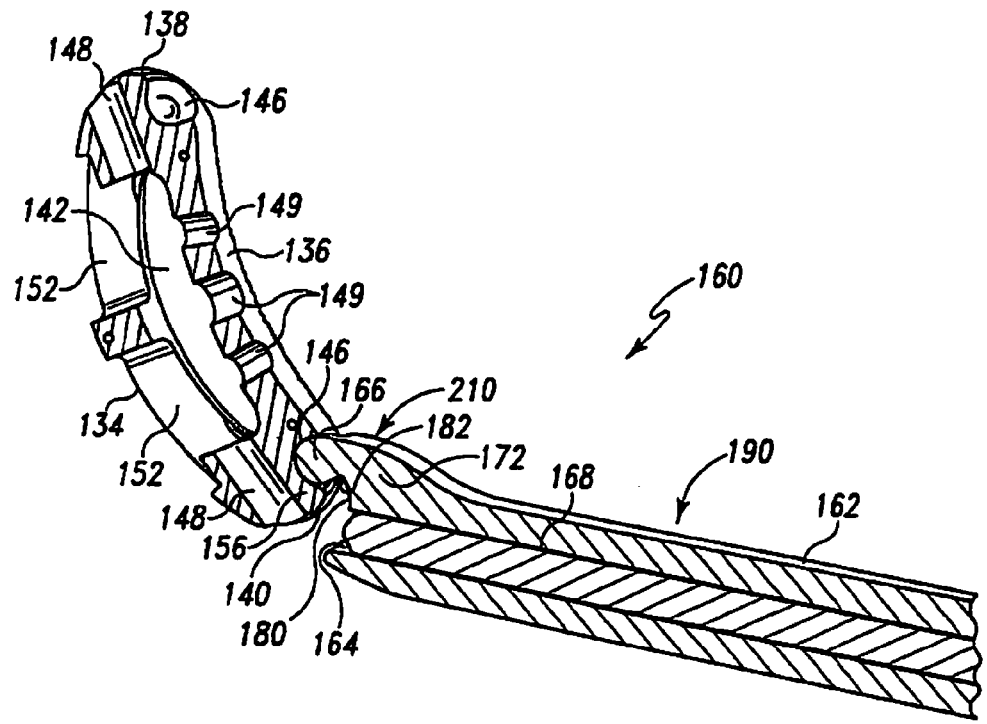
FIG. 22 is the perspective view of FIG. 21 in horizontal section through the distal portion of the inserter instrument and implant.

As shown in further detail in FIGS. 21-22, implant 130 includes an overall size and shape similar to that discussed above for implant 30. Implant 130 includes an outer wall 132 extending about a central cavity 142. Cavity 142 extends between and opens at an upper bearing surface 152 and a lower bearing surface 154. Upper and lower bearing surfaces 152, 154 contact the adjacent vertebral endplates to support the adjacent vertebrae when implanted. Surfaces 152, 154 may include pyramidally shaped teeth 150 formed thereon to facilitate engagement with the vertebral endplates and resist the implant from migrating in the disc space. Other surface features are also contemplated, including grooves, spikes, knurlings, peeks and valleys, and other projections and/or recesses.

Implant 130 includes convexly curved anterior wall portion 134 and an opposite concavely curved posterior wall portion 136. Wall portions 134, 136 are connected by a convexly curved leading end wall portion 138 and a convexly curved trailing end wall portion 140. The overall shape of wall 132 provides a banana, kidney or boomerang type shape that facilitates placement along a non-linear insertion path in the disc space. The elongated shape facilitates placement through the postero-lateral opening while minimizing the retraction of tissue and neural elements needed to accommodate insertion of the implant through the postero-lateral approach. It should be understood the leading end wall portion 138 can be a trailing end wall portion, and trailing end wall portion 140 can be a leading end wall portion, in situations where wall portion 138 is engaged with an inserter instrument and wall portion 140 is first inserted into the disc space.

A number of openings 149 in posterior wall portion 136 and elongate slots 152 in anterior wall portion 134 provide avenues for bone growth into cavity 142. Implant 130 further includes a recessed area 146 that extends into trailing end wall portion 140 adjacent posterior wall portion 136, and a receptacle 148 in trailing end wall portion 140 adjacent anterior wall portion 134. As discussed further below, the recessed area and receptacle 146, 148 are configured to receive grasper assembly 210 of inserter instrument 160. Leading end wall portion 138 can be similarly provided with recessed area and a receptacle so that implant 130 can be engaged with an inserter 160 for insertion from either direction into the spinal disc space.

Inserter instrument 160 includes shaft assembly 190 extending along longitudinal axis 161. Handle assembly 200 is at a proximal end of shaft assembly 190, and includes a handle member 172 extending transversely to longitudinal axis 161. A hub member 170 extends proximally from shaft assembly 190 along longitudinal axis 161. Hub 170 includes a slotted portion 174 formed in and opening along one side thereof. A lock driver 176 is rotatably positioned therein. Hub 170 further provides a proximally oriented platform for delivery of impaction forces to facilitate insertion of the implant engaged to grasper assembly 210.

Figure 23:
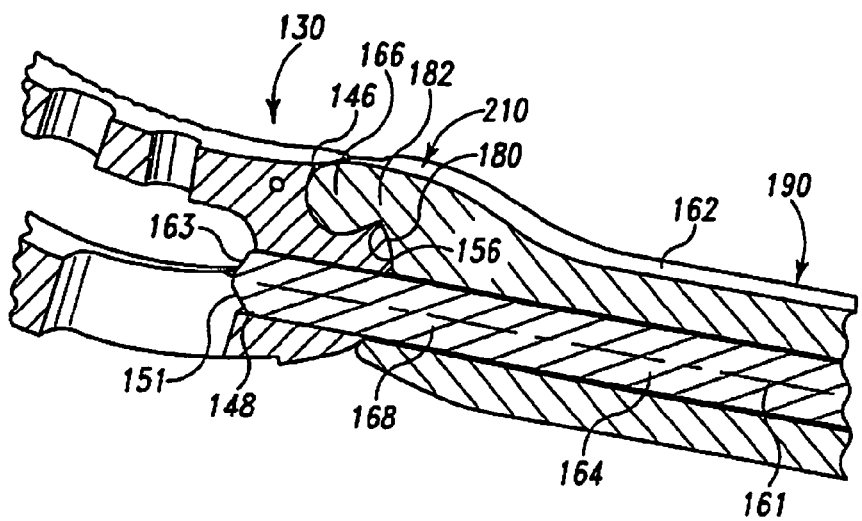
FIG. 23 is an enlarged perspective view in horizontal section showing engagement of the inserter instrument with the implant.

As shown in FIGS. 22-23, shaft assembly 190 includes a first or outer shaft 162 having a central passage 164 formed therethrough. Locking shaft 168 is received in and linearly movable in passage 164 relative to outer shaft 162. Lock driver 176 is threading engaged about a lock screw (not shown) at the proximal end of a locking shaft 168. Rotation of lock driver 176 linearly translates locking shaft 168 distally and proximally in passage 164.

Grasper assembly 210 includes a first arm 166 formed at a distal end of outer shaft 162. Outer shaft 162 includes an enlarged portion 172 to offset first arm 166 laterally from passage 164. First arm 166 includes a spherically shaped distal end portion that is rotatably received in recessed area 146. In the illustrated embodiment, recessed area 146 include a complementary spherical shape to interface with first arm 166 and allow rotation of implant 130 about first arm 166. Implant 130 is rotatable to position a distal end wall 180 of outer shaft 162 in abutting contact therewith at trailing end wall portion 140. Locking shaft 168 includes a second arm 163 formed at a distal end thereof. Locking shaft 168 and second arm 163 are distally linearly movable with lock driver 176 to advance second arm 163 into receptacle 148. The distal end of second arm 163 can be beveled to facilitate insertion into receptacle 148.

In the locking position shown in FIG. 23, locking shaft 168 prevents implant 130 from rotating about first arm 166 and holds implant 130 firmly on inserter instrument 160. The distal end of outer shaft 162 includes a recessed area 182 adjacent first arm 166, and implant 130 includes a toe 156 between recessed area 146 and receptacle 148. When second arm 163 is positioned in receptacle 148, the toe 156 is received in recessed area 182 as shown in FIG. 23. This provides a dovetail locking arrangement between implant 130 and grasper assembly 210 that implant 130 from being axially pulled or rotated relative to inserter instrument 160.

When implant 130 is positioned in the disc space, inserter instrument 160 can be disengaged therefrom by rotating lock driver 176 to proximally withdraw locking shaft 168 distally and remove second arm 163 from the receptacle 148. The inserter instrument 160 can then be withdrawn proximally from the disc space. Intrusion into tissue and neural elements in the approach to the disc space is minimized since inserter instrument 160 has the same footprint transversely to longitudinal axis 161 when engaged to implant 130 and when disengaged to implant 130. The footprint of the implant and inserter instrument assembly is also minimized during insertion since arms 163, 166 extend into implant 130 at or adjacent trailing end wall portion 140, and do not occupy space anteriorly or posteriorly of implant 130.

Figure 24:
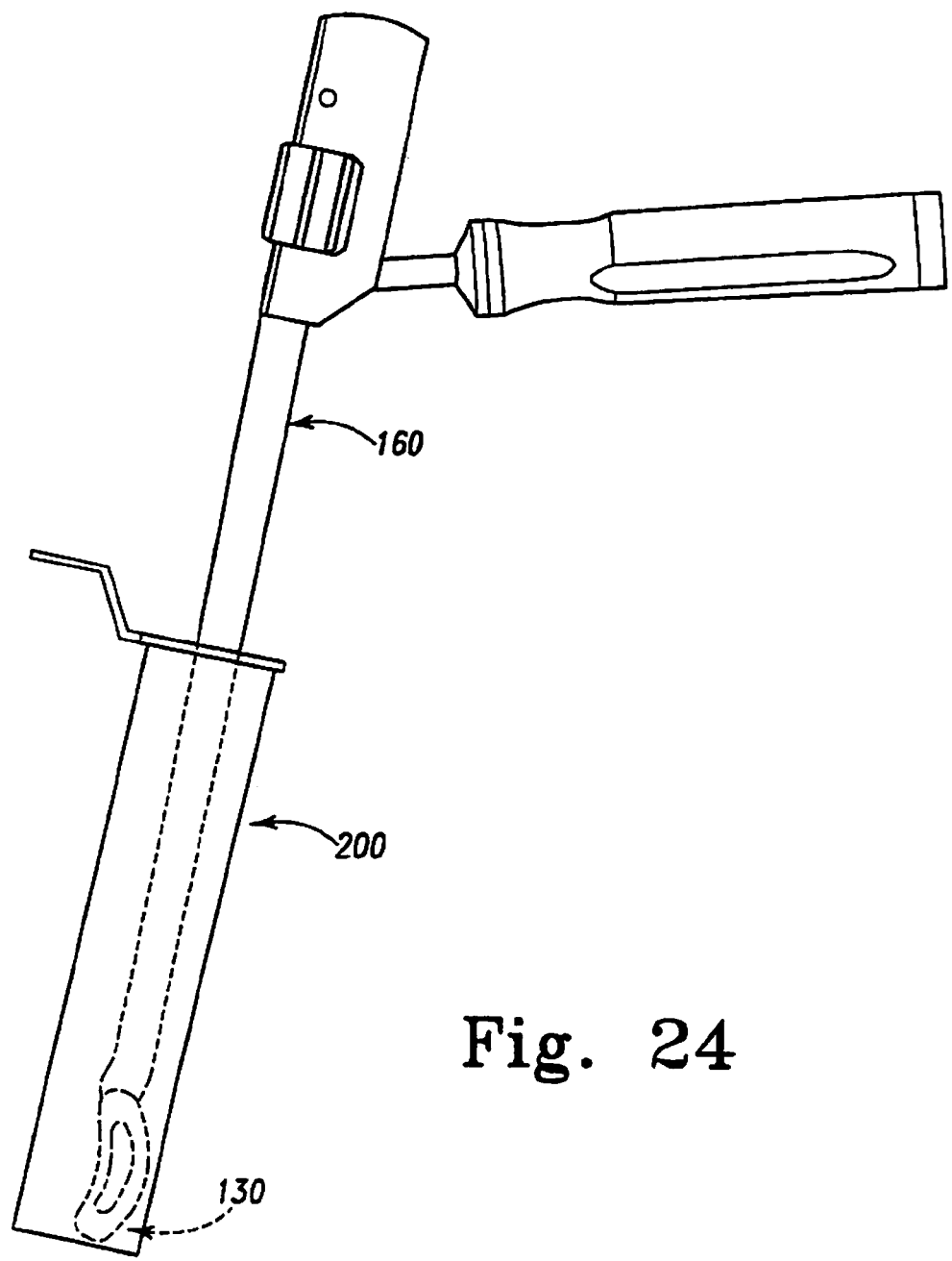
FIG. 24 is a perspective view showing the implant and inserter instrument of FIG. 20 positioned through a retractor sleeve.

The above-described instruments and methods have been disclosed with reference to use in substantially open surgical procedures. However, it is contemplated that the implants, instruments and methods may be utilized through guide sleeves or tubes, such as retractor sleeve 200 shown in FIG. 24. Such instruments can provide greater protection to adjacent tissues, to reduce the size of access incisions, to provide direct visualization of the surgical site, and/or to provide greater control of the method. The implants, instruments and methods may further be used in combination with disc space preparation and implant insertion through microscopic or endoscopic instruments that provide direct visualization of the surgical site.

The instruments discussed herein are suited for inserting an implant through a postero-lateral opening in a spinal disc space. The inserter instruments provide the surgeon the ability to control insertion of an implant into the spinal disc space from a postero-lateral approach. The inserter instruments facilitate positioning of the implant in the disc space such that the implant extends across the disc space to provide bilateral support of the adjacent vertebrae, and also facilitate positioning of the implant in the disc space along a non-linear insertion path. The inserter instruments can also be used to position multiple implants at various locations in the disc space, and also for insertion of one or more implants from other approaches to the disc space.

Implants 30, 130 can be interbody fusion devices or cages that can be packed with bone growth material or other known substance and inserted into a spinal disc space to promote bony fusion between vertebrae. Furthermore, the structural features of implant 30, 130 can have application for a disc prosthesis or a disc nucleus prosthesis that is to be inserted into the disc space. The illustrated implants 30, 130 have a boomerang or banana shape that is suited for insertion to provide bilateral support in the disc space through a unilateral, postero-lateral approach. It is also contemplated that the disc space can be accessed and prepared for implant insertion using any other known techniques and instruments and other approaches to the disc space, such as posterior, lateral, anterior or antero-lateral approaches.

Implants 30, 130 can include other shapes and also include interior bars, struts and walls. The upper and lower bearing surfaces can include double convexity to provide an intimate fit in the disc space and a profile that matches the concavity of the endplates, providing implant stability and promoting fusion. The sidewall openings and hollow interior cavity can maximize the volume available to receive bone growth material and also the contact surface area between the bone growth material and the adjacent bony structure. Furthermore, differences in heights between the upper and lower bearing surfaces at the anterior and posterior walls can be provided to establish lordosis when implants 30, 130 are inserted in the disc space.

The implants described herein can be made from any biocompatible material, including synthetic or natural autograft, allograft or xenograft tissues, and can be resorbable or non-resorbable nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites; shape-memory alloys; titanium and titanium alloys; cobalt chrome alloys; stainless steel; ceramics; and combinations thereof. Instruments described herein can be made from any suitable surgical grade material, including stainless steel, aluminum, plastics, and combinations of materials.

Any suitable osteogenetic material or composition is contemplated for placement within the cavities defined by the implants described herein. Such osteogenic material includes, for example, autograft, allograft, xenograft, demineralized bone, synthetic and natural bone graft substitutes, such as bioceramics and polymers, and osteoinductive factors. Where bony material is placed within the cavities of the implant, the material can be pre-packed into the hollow cavities before the device is implanted, or can be pushed through the wall openings after the device is in position in the spinal column. A separate carrier to hold the materials within the device can also be used. These carriers can include collagen-based carriers, bioceramic materials, such as BIOGLASS® hydroxyapatite and calcium phosphate compositions. The carrier material can be provided in the form of a sponge, a block, folded sheet, putty, paste, graft material or other suitable form. Moreover, the osteogenetic compositions contained within the implant can comprise an effective amount of a bone morphogenetic protein, transforming growth factor .beta.1, insulin-like growth factor 1, platelet-derived growth factor, fibroblast growth factor, LIM mineralization protein (LMP), and combinations thereof or other therapeutic or infection resistant agent, held within a suitable carrier material.

While the invention has been illustrated and described in detail in the drawings and the foregoing description, the same is considered to be illustrative and not restrictive in character. All changes and modifications that come within the spirit of the invention are desired to be protected.

What is claimed is:

1. An instrument for inserting a spinal implant, comprising:
   a proximal handle assembly;
   a shaft assembly extending distally from said handle assembly along a longitudinal axis, wherein said shaft assembly includes a first shaft and a second shaft, wherein said first shaft and second shaft are substantially parallel to one another forming a passage therebetween and a locking shaft movably received in said passage; and
   a grasper assembly at a distal end of said shaft assembly, said grasper assembly including first and second arms, wherein said first and second arms are remotely operable for movement relative to one another between an engaging position to engage the implant therebetween and a release position to disengage the implant from therebetween, said first arm being structured for rotatable receipt in a recessed area of the implant in said release position and said second arm being linearly movable relative to said first arm for positioning in a receptacle of the implant in said engaging position to prevent said first arm from rotating in the receptacle.

2. The instrument of claim 1, wherein said grasper assembly is structured to hold the implant in an orientation extending generally along the longitudinal axis in the initial position and in an orientation substantially obliquely oriented to the longitudinal axis in the final position.

3. A method for manipulating a spinal implant with the inserter instrument of claim 2, comprising:
   positioning a trailing end of the spinal implant adjacent first and second arms at a distal end of the inserter instrument;
   engaging the spinal implant to at least one of the first and second arms with the spinal implant generally aligned along a longitudinal axis of the inserter instrument;
   pivoting the spinal implant to a final position substantially obliquely oriented to the longitudinal axis by pivoting the first and second arms relative to the distal end of the inserter instrument while maintaining the implant in engagement with the first and second arms of the inserter instrument; and
   releasing the implant from between the first and second arms when the spinal implant is in the final position.

4. The method of claim 3, wherein positioning the trailing end of the spinal implant includes gripping the trailing end of the implant between the first and second arms of the inserter instrument.

5. The method of claim 4, wherein gripping the trailing end includes pivoting the second arm relative to and towards the first arm to grasp the trailing end of the spinal implant between the first and second arms.

6. The method of claim 3, wherein pivoting the implant to the final position includes simultaneously pivoting the first and second arms about a distal end of a shaft assembly of the inserter instrument.

7. The method of claim 3, wherein engaging the spinal implant includes positioning a distal end of the first arm in a recessed area adjacent a posterior wall of the spinal implant.

8. The method of claim 7, wherein pivoting the spinal implant to the final position includes pivoting the spinal implant about the distal end of the first arm to align a receptacle in a trailing end wall of the spinal implant with the second arm.

9. The method of claim 8, wherein engaging the spinal implant includes linearly advancing a distal end portion of the second arm into the receptacle.

10. The instrument of claim 1, wherein the first arm includes a spherically shaped distal portion that is rotatably received in a complementary shaped recessed area in the implant.

11. A spinal instrumentation system for interbody procedures, comprising:
   a spinal implant having a body including a recessed area and a receptacle;
   an inserter instrument comprising:
      a handle assembly;
      a shaft assembly extending distally from said handle assembly along a longitudinal axis; and
      a grasper assembly at a distal end of said shaft assembly, said grasper assembly including a first arm position able in said recessed area of said spinal implant and a second arm along said axis linearly movable into said receptacle of said spinal implant when said receptacle is aligned on said longitudinal axis to lock said implant in position in said grasper assembly.

12. The system of claim 11, wherein said first arm is positionable along an anterior wall portion of said implant and said second arm is positionable along a posterior wall portion of said implant.

13. The system of claim 12, wherein said body includes a recessed area along said trailing end wall portion and said anterior wall portion for receiving said first arm, and said trailing end wall portion further includes a receptacle for receiving said second arm.

14. The system of claim 11, wherein said body includes a toe between the recessed area and the receptacle configured to lock the implant to the grasper.

15. The system of claim 11, wherein said first arm includes a spherically shaped distal portion that is rotatably received in a complementary shaped recessed area in the implant.

16. The system of claim 11, wherein said shaft assembly includes an outer shaft with a passage formed therethrough, said shaft assembly further including a locking shaft moveably received in said passage.

17. The system of claim 16, wherein said locking shaft includes a lock screw at a proximal end thereof threadingly engaged with a locking driver of said handle assembly.

18. The system of claim 17, wherein said locking driver is configured to translate the locking shaft distally and proximally such that the locking shaft is translated distally to engage the implant and the proximally to disengage the implant.

19. The system of claim 16, wherein the second arm is positioned at the distal end of the locking shaft.

20. The system of claim 11, wherein said implant includes an outer surface configured to contact vertebral endplates including pyramidally shaped teeth, grooves, spikes, knurlings, peaks, valleys or combinations thereof.

* * * * *